US00PP08202P

United States Patent [19]

Bakker, Jr.

[11] Patent Number: Plant 8,202

[45] Date of Patent: Apr. 13, 1993

[54] JUNIPER PLANT—GOLD LACE VARIETY

[75] Inventor: John C. Bakker, Jr., St. Catharines, Canada

[73] Assignee: The Conard-Pyle Company, West Grove, Pa.

[21] Appl. No.: 727,227

[22] Filed: Jun. 28, 1991

[51] Int. Cl.[5] ..... A01H 5/00

[52] U.S. Cl. ..... Plt./50.2

[58] Field of Search ..... Plt./50.2

[56] References Cited

U.S. PATENT DOCUMENTS

| | | | |
|---|---|---|---|
| P.P. 2,491 | 4/1965 | Sakiyama | Plt. 50.2 |
| P.P. 3,801 | 11/1975 | Bakker | Plt. 50.2 |
| P.P. 5,014 | 3/1983 | Girard | Plt. 50.2 |
| P.P. 6,149 | 4/1988 | Strohsahl | Plt. 50.2 |

*Primary Examiner*—James R. Feyrer

*Attorney, Agent, or Firm*—Burns, Doane, Swecker & Mathis

[57] ABSTRACT

A new and distinct variety of Chinese Juniper plant of the Golden Pfitzer type named Gold Lace is provided. The new variety is a spontaneous mutation of Juniperus Golden Pfitzer (non-patented in the United States). The new variety grows more slowly, exhibits a more prostrate growth habit, and forms attractive deeper, richer, and more persistent golden foliage coloration (as illustrated). The new variety, because of its distinctive appearance is particularly suited for growing as a specimen plant, as a foundation planting, or as a decorative mass planting. Dense compact and soft-textured plants requiring very little maintenance are provided which impart vivid coloration to the modern landscape throughout the season.

3 Drawing Sheets

SUMMARY OF THE INVENTION

The present invention comprises a new and distinct variety of *Juniperus chinensis*, and hereinafter is referred to by the variety name Gold Lace.

The new Gold Lace variety is a spontaneous mutation of unknown causation which was discovered and carefully preserved during the course of plant selection work which was conducted by me during May, 1983. A single branch of a single plant of Juniperus Golden Pfitzer (non-patented in the United States) present in production fields at St. Catharines, Ontario, Canada, was found to exhibit a distinctive foliage appearance unlike that exhibited by all other plants being grown in the area. Had I not discovered, carefully studied, and preserved this new variety, it would have been lost to mankind.

It was found that the new variety of *Juniperus chinensis:*

(a) grows more slowly than Juniperus Golden Pfitzer,
(b) exhibits an attractive, deeper and more persistent golden foliage coloration than Juniperus Golden Pfitzer which extends to near the center of the plant, and
(c) exhibits a compact more prostrate growth habit than other golden *Juniperus chinensis* varieties.

The golden foliage coloration is deeper, richer, and more persistent than that of its parent and most other golden forms of *Juniperus chinensis*. The gold coloration is present almost to the center of the plant and is retained to a greater extent throughout the summer. Also, the slower growth and more prostrate growth habit enables the grower to better retain the desired overall appearance of the planting over an extended period of time.

Plants propagated from the original mutation after four years have spread in width to over four feet and are approximately 18 inches in height. The winter hardiness of the new variety has been confirmed at both St. Catharines, Ontario, Canada, and at West Grove, Pa., U.S.A., over the past four years.

The plants of the new variety have been found to take shearing well. The golden foliage coloration is the most vivid and covers more of the plant when grown in the full sun. As the amount of exposure to direct sunlight is decreased, the golden foliage coloration will decrease, and may substantially disappear when plants of the new variety are grown in full shade.

Asexual propagation of the new variety over a number of seasons by cuttings as performed at St. Catharines, Ontario, Canada, and at West Grove, Pa., U.S.A., have demonstrated that the characteristics of the new variety as disclosed herein are firmly fixed and are retained through successive generations of asexual propagation. For instance, the new variety can be readily propagated through the use of hardwood cuttings during the winter. Alternatively, during the summer cuttings of new growth can be placed under mist. The new plants produced from cuttings have been found to grow vigorously, are true to type, and have encountered few problems from insects or diseases. There have been no observed reversions of the new variety to the parent variety during the entire period of its observation.

The new variety, because of its distinctive foliage coloration and growth habit, was found to be particularly suited for growing as a specimen plant, as a foundation planting, or as a decorative mass planting. It lends itself well to conventional production methods and cultural practices when grown either in the field or in containers and meets the demands of the modern landscape. Dense compact soft-textured plants requiring very little maintenance are provided which impart an attractive, vivid coloration to the landscape throughout the season.

The new variety, in view of its novel combination of characteristics, can be readily distinguished from all other golden *Juniperus chinensis* varieties and all other *Juniperus*×*media* Pfitzeriana Aurea. For instance, the Golden Lace variety differs from the Bakaurea variety (U.S. Plant Pat. No. 3,801) in that the new variety exhibits a different growth habit, the golden foliage coloration is more vivid and extends more towards the base of the branches, the golden foliage coloration remains bright longer into the summer, and the golden foliage coloration is better retained throughout the winter unlike the brownish-green foliage coloration which commonly is assumed by the Bakaurea variety during the winter. When the new variety is grown side-by-side with the Bakaurea variety, it clearly retains its golden coloration longer than the Bakaurea variety.

BRIEF DESCRIPTION OF THE PHOTOGRAPHS

The accompanying photographs show as nearly true as it is reasonably possible to make the same, in color illustrations of this character, typical specimens of the plant and plant parts of the new variety. The plants depicted in the photographs were grown at West Grove, Pa., U.S.A.

Figure 1:
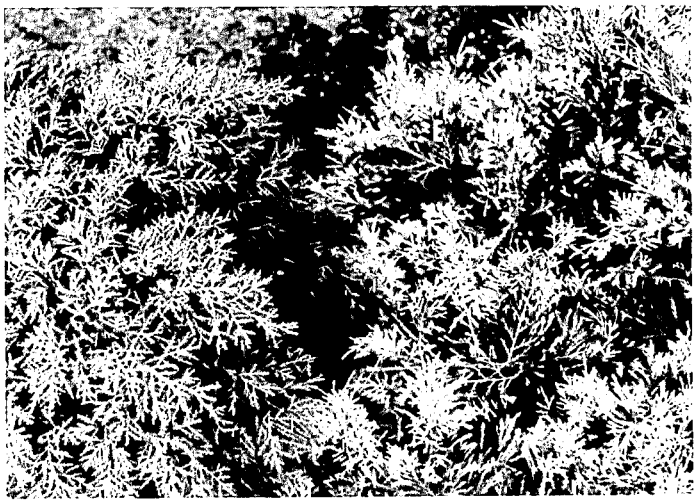
FIG. 1 illustrates the typical appearance of the new variety following three seasons of growth wherein the coloration during the spring is shown on the right at "E" and the coloration during the early summer is shown on the left at "D".
Figure 2:
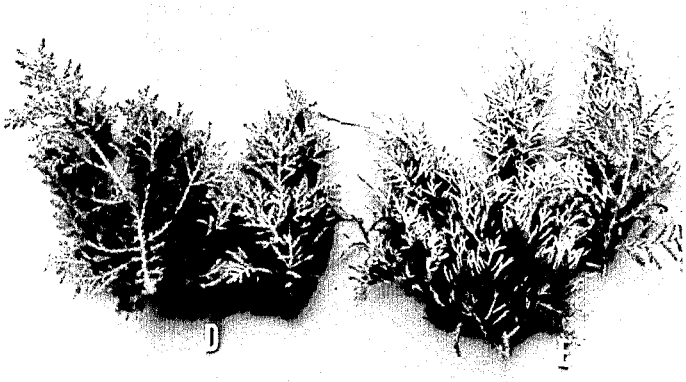
FIG. 2 illustrates the typical appearance of the foliage of the new variety on the upper and under surfaces wherein the coloration during the mid-spring is shown on the right at "E" and the coloration during the early summer is shown at the left at "D".
Figure 3:
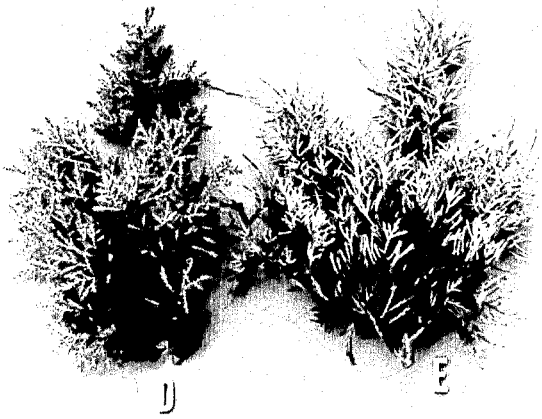
FIG. 3 illustrates the typical appearance of the foliage of the new variety on the upper surface only wherein the coloration during the mid-spring is shown on the right at "E" and the coloration during the early summer is shown on the left at "D".
Figure 4:
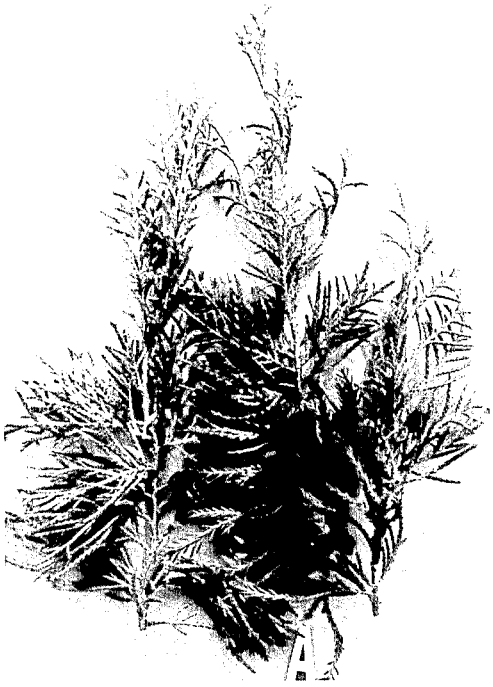
FIG. 4 illustrates the typical appearance of the foliage of the new variety on the upper and under surfaces during late winter/early spring.
Figure 5:
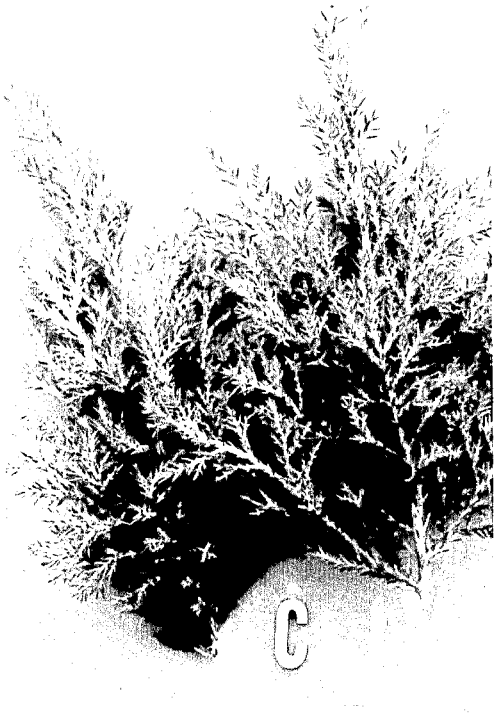
FIG. 5 illustrates the typical appearance of the foliage of the new variety on the upper and under surfaces during early summer.
Figure 6:
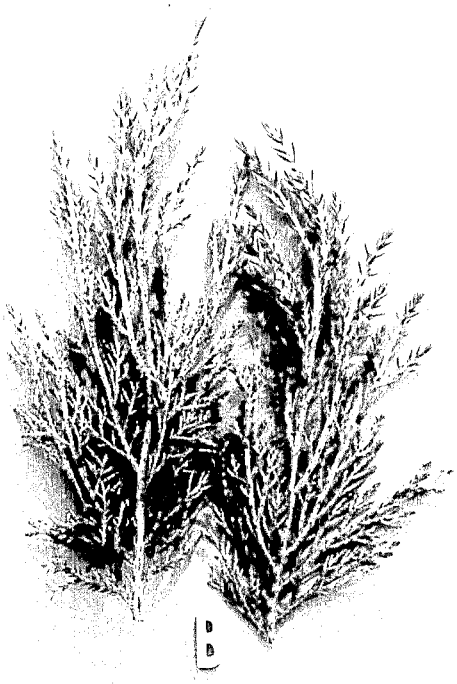
FIG. 6 illustrates the typical appearance of the foliage of the new variety on the upper and under surfaces during late summer.

In FIGS. 1, 2, and 3 the exhibition of early summer coloration was obtained by forcing the plant while temporarily placed in a greenhouse with the control of the temperature and the day length.

DETAILED DESCRIPTION

The chart used in the identification of colors described hereafter is the R.H.S. Colour Chart of The Royal Horticultural Society, London, England. The plants described were grown in full sun during 1990 at West Grove, Pa.

Classification: *Juniperus chinensis*, Gold Lace variety.

Foliage:

*Type.*—Juvenile, needle shaped.

*Spring-summer color of new leaves at growing tips of primary and secondary branches.*—Upper side: Initially Yellow Group 12A in the spring, turning to Yellow Group 11A in early summer, and then turning to Green Group 138B during mid-summer. Lower side: At point of attachment Yellow Group 7B in the spring, and turning to Yellow-Green Group 144B during the summer. Tip of Leaf: Yellow Green Group 144B in spring, and turning to Green Group 138B during the summer.

*General appearance of new leaves when unfolding during the spring.*—Upper side: Green Group 138B. Lower side: Yellow-Green Group 144B. At point of attachment: Yellow Group 7C in spring, turning initially to Yellow Group 12A, and subsequently turning to Yellow Group 11A in the summer. At center of the leaf: Yellow-Green Group 144B.

*General appearance of foliage during spring.*—Upper side: Yellow Group 11A mixed with Yellow-Green Group 145B. Lower side: Green Group 138B.

*General appearance of foliage during early summer.*—Upper side: Yellow Group 11A mixed with Yellow-Green Group 145A.

*General appearance of foliage during mid-summer.*—Upper side: Yellow-Green Group 145A mixed with Yellow Group 11A. Lower side: Yellow-Green Group 144B.

*Winter color of tips of primary and secondary branches when exposed to weather.*—Upper side: Greyed-Yellow Group 162A. Lower side: Greyed-Yellow Group 162B mixed with Yellow-Green Group 153D, and turning to Green Group 138B near the point of attachment.

*Winter general appearance of foliage on the outside of the plant.*—When not protected from weather: Greyed-Yellow Group 162A mixed with Greyed-Yellow Group 162B. When protected from weather: Yellow-Green Group 151A when viewing the lower side of a branch, and turning to Green Group 138A at the center of the plant.

*Winter color of leaves on the inside of the plant when protected from the weather.*—At upper side of branch: Yellow-Green Group 146C, and turning to Green Group 138A during early spring. At point of attachment: Yellow-Green Group 146A. At lower side of branch: Yellow-Green Group 146A.

*Winter general appearance of last season's foliage.*—Yellow-Green Group 146B, and turning to Green Group 138B in early spring.

*Winter general appearance of mature foliage (prior to last season).*—Yellow-Green Group 146A, and turning to Green Group 138B in early spring.

Branches:

*Summer coloration.*—On growing tips of main branches: Yellow Group 12A, and turning to Yellow Group 11A. On side shoots of main branches: Green Group 138A. On maturing wood: Yellow-Green Group 144B on prior season's growth. On mature wood: Greyed-Orange Group 177C mixed with Greyed-Purple Group 187A on the upper side, and Greyed-Purple Group 187A on the lower side. On secondary branches: Yellow-Green Group 145A when protected from the weather and Yellow-Green Group 145B when exposed to the weather.

*Winter coloration.*—On outer branches: Greyed-Orange Group 165B on the upper side and Greyed-Orange Group 177A mixed with Greyed-Orange 177B on the lower side. On mature branches: Greyed-Orange Group 166B on upper side and Greyed-Purple Group 187A on lower side. On old wood: Greyed-Orange Group 177A on the upper side and Greyed-Purple Group 187A on the lower side.

General Appearance of Entire Plant:

*End of winter.*—At center of plant: Yellow-Green Group 151A. At outer parts of plant: Yellow-Green Group 151B.

*Mid-spring.*—At center of plant: Yellow-Green Group 147B. At outer parts of plant: Yellow Group 12B.

*Summer.*—At center of plant: Green Group 137B. At outer parts of plant: Yellow-Green Group 145 mixed with Yellow Group 11A.

Plants of the new variety have been found to grow more slowly than plants of the parent variety. More specifically, the terminal growth of the new variety during one year commonly measures approximately 6 to 8 inches, and that of the parent variety commonly measures 10 to 15 inches.

Plants of the new variety are always smaller than those of the parent variety at the same age. For instance, the height of the new variety commonly will be slightly less than that of the parent variety, and its width commonly will be approximately 40 to 50 percent less than that of the parent variety when comparing plants of the same age.

When the seasonal foliage color change of the new variety is compared to that of the parent variety, it is found that the new variety commonly exhibits a far deeper golden coloration at all times during the growing season. The overall appearance of the new variety always is brighter and more golden than that exhibited by its parent. Also, the deeper golden coloration of the new variety extends considerably farther into the interior of plant than the less golden coloration of its parent.

While many gold Junipers exhibit a somewhat golden appearance on the extremities of the current growth, the deeper golden coloration of the new variety is found to persist to almost the center of the plant particularly when grown in full sun. The same observations have been made even when a plant of the new variety is in the dormant state. Then the new variety commonly will exhibit foliage which is significantly more uniformly golden or yellow than its parent.

The photographs discussed previously show the appearance of both mature and juvenile foliage. It has been observed that the adult foliage of the new variety tends to be more golden in coloration and to maintain such golden coloration for a longer period of time than does the juvenile foliage. The new growth formed in the spring commonly assumes a bright yellow to gold coloration and gradually changes with maturity in some parts of the plant to a golden-green coloration which when blended with the coloration of the stems conveys an overall appearance of a dull bronze-brown at some areas of the plant especially when the plant is dormant.

No fruit has been observed on plants of the new variety during observations to date.

I claim:

1. A new and distinct variety of *Juniperus chinensis*, substantially as herein shown and described, which:

(a) grows more slowly than Juniperus Golden Pfitzer,
(b) exhibits an attractive, deeper and more persistent golden foliage coloration than Juniperus Golden Pfitzer which extends to near the center of the plant, and
(c) exhibits a compact more prostrate growth habit than other golden *Juniperus chinensis* varieties.

* * * * *